United States Patent [19]

Sakamoto et al.

[11] Patent Number: 4,737,503

[45] Date of Patent: Apr. 12, 1988

[54] METHOD FOR INHIBITING THE RELEASE OF HISTAMINE

[75] Inventors: Seizaburo Sakamoto, Chestnut Hill; Katsumi Sugiyama, Boston, both of Mass.

[73] Assignee: Vipont Laboratories, Inc., Fort Collins, Colo.

[21] Appl. No.: 916,552

[22] Filed: Oct. 8, 1986

[51] Int. Cl.$^4$ ............................................. A61K 31/44
[52] U.S. Cl. ...................................................... 514/279
[58] Field of Search ......................................... 514/279

[56] References Cited

PUBLICATIONS

Merck Index, 9th Ed., (1976), pp. 1082–1083.

*Primary Examiner*—Stanley J. Friedman
*Attorney, Agent, or Firm*—Eric P. Schellin

[57] ABSTRACT

The present invention deals with the inhibition of histamine release from mammalian mast cells by contacting such cells with sanguinarine, a benzophenanthridine alkaloid.

6 Claims, 1 Drawing Sheet

METHOD FOR INHIBITING THE RELEASE OF HISTAMINE

FIELD OF THE INVENTION

The present invention relates to a method for controlling the release of histamine from mast cells.

BACKGROUND OF THE INVENTION

Benzo-c-phenanthridine alkaloids can be extracted from plants of the familiar Papaversease, Fumariaceae, and Berberidaceae. Some of the plants of these familiar includes *Sanguinaria canadensis, Macleaya cordata, Bocconia frutescens, Carydalis sevctcozii, C. ledebouni, Argemone mexicanus,* and *Chelidonium majus.* Among the most important benzo-c-phenanthridine alkaloids obtained from these plants are sanguinarine, chelirubine, macarpine, allocryptopine, protopine, hemochelidonene, sanguilatine, sanguiribine, and chelerythrine.

The best known of these alkaloids is sanguinarine, which has been extracted from the *Sanguinaria canadensis* plant (otherwise known as bloodroot, teteroot, redroot, puccoon, etc.) a perennial herb native to North America. The sanguinaria plant and its juices have been used for various proposes in pre-historic and historic times. The plants have been used, in particular, as a folk remedies. The plants have generally been used while, either undried (fresh) or dried, and the usual procedure is to powder the dried plant and mix it with a carrier. This folk remedy has been tried for such conditions as bronchitis, dysentery, ringworm and a substantial list of other ailments.

The pure chemicals sanguinarine, chelerythrine, protopine, chelerubine, berberine, chelilutine, sanguilatine, macarpine, sanguirubine and allocryptopine can be isolated from plants other than Sanguinaria. They are also available, although rarely, from some chemical supply houses. Semi-purified forms of the alkaloids are commercially available, and these are generally referred to as sanguinarine nitrate and sanguinarine sulfate. These compounds are the salts of the mixed alkaloids of the plant Sanguinaria: mainly sanguinarine, chelerythrine, and protopine. While few references can be found in the literature regarding the usage of any of the pure benzo-phenanthridine alkaloids, plants containing such compounds have been used for a wide variety of medical ailments.

The alkaloid sanguinarine in solution has been shown to have some antifungal and antiprotozoan properties. The sanguinarine is applied as an emulsion topically to fungal infections. The antibacterial activity of sanguinarine has been found to vary with attached radicals, and various salts of sanguinarine have been shown to have some activity. The hydrochloride and the sulfate salts have been found to have some activity against certain bacteria at certain concentrations. Sanguinarine nitrate is reported to have some bacteriostatic action against various types of bacteria.

The use of an extract of *Sanguinaria canadensis* as an ingredient in oral cleaning preparation, in particular, toothpaste, is disclosed in U.S. Pat. No. 4,145,412.

This extract is produced by treating a finely cut or ground bloodroot with an organic solvent, such as methanol. The bloodroot is thoroughly stirred with several volumes of the solvent, and is maintained in the solvent for 24 hours or more, at a temperature of about 60° C. Subsequently, the solution is filtered and the methanol is evaporated. The residue is dissolved in chloroform, treated with concentrated hydrochloric acid, filtered and then dried. These dried extract is generally taken up in warm glycerine (65° C.) for mixing with a carrier.

High purity of the sanguinarine can be obtained by various methods such as exemplified from U.S. patent application Ser. No. 822,967 filed Jan. 28, 1986 and Ser. No. 827,143 filed Feb. 7, 1986, now abandoned, incorporated herein by reference.

SUMMARY OF THE INVENTION

The present invention therefor deals with the inhibition or suppression of histamine release from mammalian mast cells by contacting such cells with sanguinarine, a benzophenanthridine alkaloid. In giving evidence of the invention it has been discovered that Sanguinarine (1-10 $\mu$M) inhibited histamine release stimulated by compound 48/80, a well known histamine release agent. This inhibitory action was also found when histamine release was induced by other known histamine releasers, such as concanavalin A, histidine-rich polypeptide (Fraction-A), and calcium-ionophore A 23187, while this was not the case with a well known surfactant Triton X-100 (octylphenoxy polyethryethanol). It is believed that the sanguinarine acts as a stabilizer of the membrane of the mast cells.

DETAILED DESCRIPTION OF THE INVENTION

Figure 1:
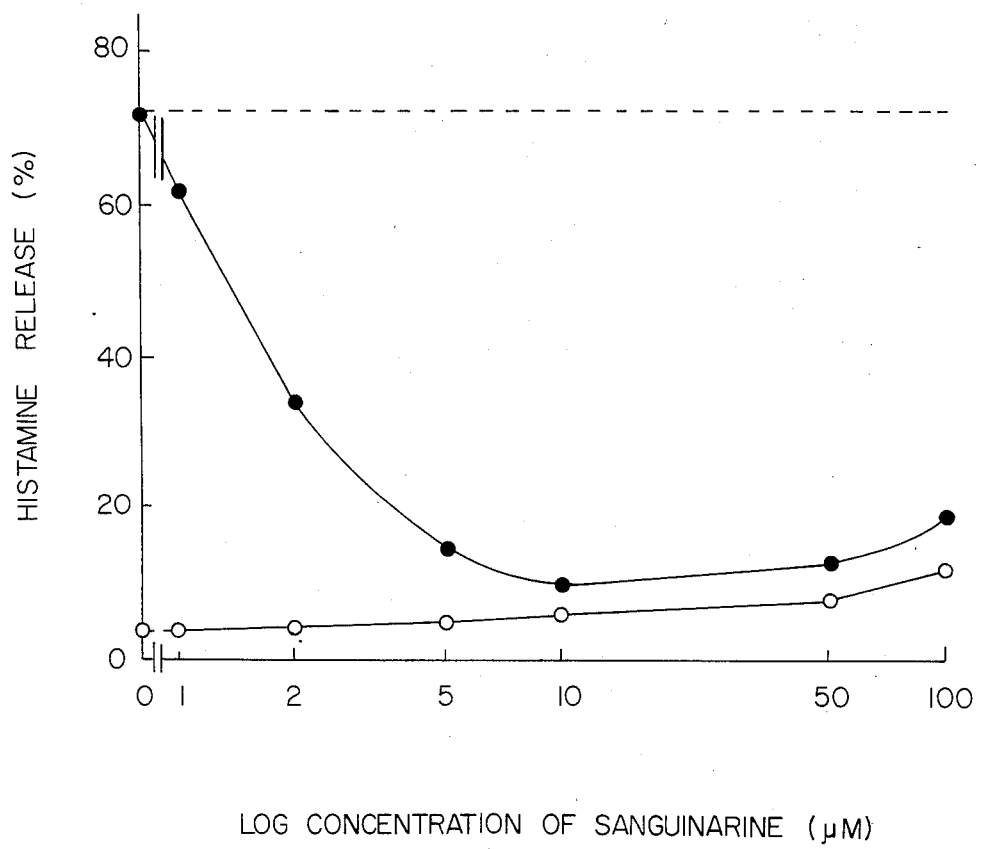

Sanguinarine heretofore stated is a benzophenanthridine alkaloid extracted, for example, from the rhizomes of the plant *Sanguinaria candensis;* as seen in American Pharmaceutical Association, National Formulary, 7th Revision (1940) pp. 191, 368 and 416. It has been shown that sanguinarine exhibits various biological activities such as antimicrobial activity; as seen in Johnson, C. C. Johnson, G. and Poe, C. F. (1952) Acta Pharmacol, Toxicol. 8, 71-78; and Dzink, J. L. and Scransky, S. S. (1985) Antimicrobial Agents and Chemother. 27, 663-665. There is evidence that it also inhibits Na, K-ATPase, as seen in Straub, K. D. and Carver, P. (1970) Biochem. Biophys. Rec. Commun. 62, 913 and 922. It has also shown cation-transport, as seen in Cala, P. M., Norby, J. G. and Toteson, D. C. (1982) J. Membrane Biol. 64, 23-31. It has been shown to inhibit yeast respiration, as seen in Vallejos, R. H. and Roveri, O. A. (1972) Biochem. Pharmacol. 21, 2179-3182. More recently it has also been found that sanguinarine has anti-plaque activity as seen in Southard, G. L. Boulware, R. T., Walborn, D. R., Groznik, W. J., Throne, E. E. and Yankell, S. L. (1981). Am. Dent. Assoc. 108, 338-341. Sanguinarine also has anti-inflammatory activity as demonstrated in Lenfeld, J., Kroutil, M., Marsalek, E., Slavik, J., Preininger, V. and Simanak, V. (1981) Planta Med. 43, 161-165. Finaly as perhaps the latest finding it is now known that sanguinarine demonstrates significant inhibition of bone resorption in vitro, as seen in Cowen, K. D., Sakamoto, S., Sakamoto, M. and Southard, G. L. (1986) J. Dent. Res. 65, 246.

In exemplifing the invention, mast cells were isolated from the peritoneal fluid of male Wistar rat as described in Sugiyama, K. (1971) Japan J. Pharmacol. 21, 209-226. The mast cells were suspended in a phosphate buffered saline solution consisting of 154 mM sodium chloride, 2.7 mM potassium chloride, 0.9 mM calcium chloride, 6.7 mM $KH_2PO_4$-$Na_2HPO_4$, (pH 7.3), and 0.01% bovine serum albumin obtained from Sigma.

For the determination of histamine release and its inhibition by sangainarine., mast cells at a cell density of $10^5$ cells/ml suspended in 0.5 ml of phosphate-buffered saline, were incubated at 37° C. for 10 minutes with histamine releasers, more about which is stated below. Sanguinarine was added 5 minutes before the specific histamine releaser. After the action was terminated by the addition of 1.5 ml of ice-cold phosphate-buffered saline solution, the samples were centrifuged at 2,000 rpm for 15 minutes. The histamine in the supernatants and precipitates was determined according to the method of Shore, P. A., Burkhalter, A. and Cohn N. H. (1959) J. Pharmacol, Exp Ther. 127, 182–186. Release of histamine was expressed as a percentage of the total cell content. Percentages of inhibition by sanguinarine were measured according to the following equation:

$$\text{Inhibition \%} = \left(1 - \frac{\text{Histamine released from mast cells (with Sanguinarine)}}{\text{Histamine released from mast cells (without Sanguinarine)}}\right) \times 100$$

The sanguinarine chloride was provided from Vipont Laboratories Inc. and is manufactured in the manner disclosed in U.S. patent application Ser. No. 822,967 filed Jan. 28, 1986 and is incorporated herein in its entirety by reference. Histidine-rich polypeptide fraction A, known as HRP(F-A) was purified from human saliva in accordance with the procedure of Sugiyama, K., Suzuki, Y and Furuta, H (1985) Life Sciences. 37, 475–480. The comparison was carried out with known histamine releasers, namely 48/80; Concanavalin A; calcium-ionophore A23187. These releasers may be obtained from Sigma Co.

In the results it was noted that 48/80 induced histamine release from mast cells was inhibited by sanguinarine in a dose-dependent manner as can be seen from FIG. 1; wherein the $IC_{50}$ (inhibition concentration) was about 2 $\mu$M. Histamine release induced by sanguinarine itself was not apparent in a concentration less than 100 $\mu$M. The inhibitory effect of sanguinarine was also observed in the histamine release stimulated by Concanavalin A, histadine-rich polypeptide and Ca-ionophore A 23187, but not in the histamine release stimulated by Triton X-100 (Table 1).

It has been recognized that histamine release stimulated by compound 48/80 from mast cells is initiated by the fusion of plasma and granule membrane (exocytosis) as discussed by Uvnas, B. (1974) Fed. Proc. 33, 2172–2176. Concanavalin A. stimulates histamine release from mast cells in the presence of phosphatidylserine and calcium ions, discussed by Sugiyama, K., Sasaki, J. and Yamasaki, H. (1975) Japan. J. Pharmacol. 25, 485–487. Calcium-ionophore A 23187 also releases histamines dependent upon the external Calcium ions. On the other hand, histamine release evoked by compound 48/80 and histidine-rich polypeptide is independent of extracellular calcium. Sanguinarine markedly inhibited histamine release induced by a variety of different agents except Triton X-100 (a detergent). These observations suggest that sanguinarine may not inhibit a calcium-dependent mechanism required for the initiation of histamine release.

It has been reported in Pearce, F. L., Atkinson, G., Ennis, M., Trench, A., Weston, P. M. and While, J. R. (1979) in "The Mast Cell" (Pepys, J. and Edwards, A. M., ed.) pp 69–75, Pitman Medical Publishing Co. Ltd, England that anti-allergy drugs such as theophylline and cromoglycate inhibited the histamine release produced by compound 48/80, calcium-ionophore A23187, and basic peptide 401, (a bee venom); the latter mentioned in the immediately forgoing literature article. They indicated that the $IC_{50}$ of these drugs was in a 0.01–1 mM concentration range. These values are about 10 to 100 times less active than sanguinarine inhibited histamine release. It has also been shown in Yamasaki, H. and Saeki K. (1967) Arch, int. Pharmacodyn. 168, 166–179 that compound 48/80 induced histamine release was inhibited by the anti-inflammatory agents, indomethacin, sodium salicylate, and hydrocortisone. The $IC_{50}$ for those agents was 75 $\mu$M, 1.6 mM and 2.1 mM, respectively. Thus, in comparison with the $IC_{50}$ of these drugs, sanguinarine inhibits histamine release at very low concentrations.

It is pointed out that the mechanisms by which sanguinarine inhibits histamine release are at present unknown. It is speculated that sanguinarine acts as a stabilizer of membrane activities relating to the physical chemical nature of exocytosis involving transfer of the inner granules to the outside.

TABLE 1

Inhibition by Sanguinarine of Histamine Release from Rat Isolated Mast Cells

| Releasing agents (Conc.) | Sanguinarine ($\mu$M) | Histamine Release (%) | % Inhibition |
|---|---|---|---|
| Compound 48/80 | — | 72.3 | 78.7 |
| (0.5 $\mu$g/ml) | 5 | 15.4 | |
| Con A* | — | 62.9 | 56.6 |
| (10 $\mu$g/ml) | 5 | 27.3 | |
| A23187 | — | 57.7 | 63.4 |
| (1 $\mu$M) | 5 | 21.1 | |
| HRP | — | 57.6 | 69.4 |
| (16 $\mu$M) | 5 | 17.6 | |
| Triton X-100 | — | 84.8 | −10.6 |
| (0.01%) | 5 | 93.8 | |

*in the presence of phosphatidylserine (10 $\mu$g/ml)

With regard to FIG. 1, inhibition by sanguinarine of histamine release induced by compound 48/80 is shown. The mast cells were incubated at 37° C. for 10 minutes with and without compound 48/80 in the presence of sanguinarine in varying concentrations. (•) Sanguinarine with compound 48/80 (0.5 $\mu$g/ml), (0) Sanguinarine without compound 48/80.

What is claimed is:

1. A method for inhibiting the release of histamine from mammalian mast cells comprising contacting said mast cells with a histamine inhibiting amount of benzo-c-phenanthridine alkaloid.

2. The method of claim 1 wherein the benzo-c-phenanthridine alkaloid is sanguinarine chloride.

3. The method of claim 2 wherein the sanguinarine chloride is in a diluent.

4. A method of controlling the release of histamine from mammalian mast cells comprising contacting said mast calls with a histamine inhibiting amount of benzo-C-phenothridine alkoloid.

5. The method of claim 4 wherein the benzo-c-phenanthridine alkaloid is sanguinarine chloride.

6. The method of claim 5 wherein the sanguinarine chloride is in a diluent.

* * * * *